United States Patent [19]

Singer et al.

[11] Patent Number: 5,638,832
[45] Date of Patent: Jun. 17, 1997

[54] PROGRAMMABLE SUBCUTANEOUS VISIBLE IMPLANT

[75] Inventors: Andrew J. Singer, Palo Alto; Sean White, San Francisco, both of Calif.

[73] Assignee: Interval Research Corporation, Palo Alto, Calif.

[21] Appl. No.: 477,096

[22] Filed: Jun. 7, 1995

[51] Int. Cl.$^6$ .................................................. A61B 19/00
[52] U.S. Cl. .................................................. 128/899
[58] Field of Search .............................. 128/897–899, 128/654

[56] References Cited

U.S. PATENT DOCUMENTS

| | | |
|---|---|---|
| 4,233,964 | 11/1980 | Jefferts et al. ............... 128/899 |
| 5,041,826 | 8/1991 | Milheiser . |
| 5,074,318 | 12/1991 | Campbell et al. . |
| 5,205,286 | 4/1993 | Soukup et al. ............... 128/899 |
| 5,322,034 | 6/1994 | Willham et al. . |
| 5,324,940 | 6/1994 | Ekstrom . |
| 5,482,008 | 1/1996 | Stafford et al. ............... 128/899 |

*Primary Examiner*—Lee S. Cohen
*Assistant Examiner*—John P. Lacyk
*Attorney, Agent, or Firm*—Brooks & Kushman

[57] ABSTRACT

A subcutaneous implant for displaying various re-programmable information or decorative patterns beneath the surface of the skin of a person or an animal. A biologically inert subcutaneous implant is constructed of a flexible material so as to conform to the skin's surface. The subcutaneous implant includes a battery for providing power to the implant. The subcutaneous implant also includes a receiver for receiving programming information from a user, and a display for displaying the programming information through the skin.

19 Claims, 2 Drawing Sheets

PROGRAMMABLE SUBCUTANEOUS VISIBLE IMPLANT

TECHNICAL FIELD

This invention relates to inert visible implants. In particular, this invention relates to inert visible implants capable of being reprogrammed to display various different information in any desired manner.

BACKGROUND ART

There are several known electronically triggered identification implants that are used for livestock and other animal identification. One known device described in U.S. Pat. No. 5,322,034, issued to Willham et al., discloses an electronic identification and data storage module which is implanted beneath the skin of an animal. The electronic module is read and controlled by an external reading and recording device. The electronic module also includes memory for storing various records and for identifying the animal.

A system for indicating an identification marker is disclosed in U.S. Pat. No. 5,074,318, issued to Campbell et al. Campbell et al. discloses an apparatus for implanting a marker into an animal for identification purposes. The marker is a capsule having therein an electronic transponder containing identification information about the animal. In one embodiment, the marker is formed of a smooth material, such as glass.

A third known identification system is disclosed in U.S. Pat. No. 5,041,826, issued to Milheiser. Milheiser discloses a passive integrated transponder (PIT) attached to or embedded in an item to be identified. The embedded device is a passive electronic circuit which is inductively coupled to an interrogator to exchange information.

A fourth known identification system is disclosed in U.S. Pat. No. 5,324,940, issued to Ekstrom. Ekstrom discloses implantable visible tags which are placed in transparent tissue of a macroorganism, such as a fish. The tags include fluorescent dyes or pigments which are used to identify the particular macro-organism. Encoded information is obtained from the tags by measuring the spectrum of light emitted by the fluorescent colorants.

The known prior art fails to disclose an implantable device that displays various information such as, identification information, medical information, decorative patterns, etc. Still further, the known prior art fails to disclose an implantable device which may be reprogrammed so as to change the current display.

DISCLOSURE OF THE INVENTION

It is thus a general object of the present invention to provide a subcutaneous implant, inserted beneath the skin of a person or an animal, which displays various information for external reading.

It is another object of the present invention to provide a subcutaneous implant capable of being reprogrammed so as to change the information currently displayed beneath the skin of a person or an animal.

In carrying out the above objects and other objects, features and advantages, of the present invention, a subcutaneous implant is provided for displaying information or decorative patterns beneath the surface of the skin of either a person or an animal.

The subcutaneous implant is encapsulated so that it may be safely implanted beneath the skin of a person or an animal. The subcutaneous implant is also flexible so that it conforms to the skin's surface. The subcutaneous implant includes a receiver for receiving programming information from a user. The programming information may be medical information, identification information, decorative patterns, etc. The subcutaneous implant further includes a display, such as a liquid crystal display, for displaying the programming information. Finally, the subcutaneous display includes a battery for providing power to the receiver and the display.

The above objects, features and advantages of the present invention, as well as others, are readily apparent from the following detailed description of the best mode for carrying out the invention when taken in connection with the accompanying drawings.

BRIEF DESCRIPTION OF THE DRAWING

A more complete appreciation of the invention and many of the attendant advantages thereof may be readily obtained by reference to the following detailed description when considered with the accompanying drawings in which like reference characters indicate corresponding parts in all of the views, wherein.

BEST MODE FOR CARRYING OUT THE INVENTION

Figure 1:
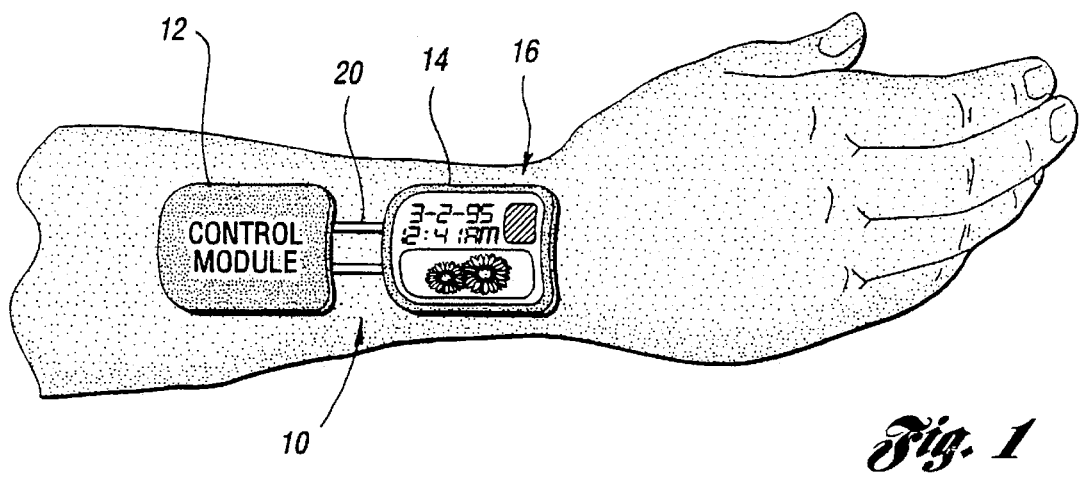
FIG. 1 is a perspective view of an embodiment of the present invention implanted shallowly beneath the skin of a person.

FIG. 1 provides an illustration of an embodiment of a subcutaneous implant 10 in accordance with the present invention. The subcutaneous implant 10 includes a control module 12 which provides a signal representative of an image to be visually displayed. The subcutaneous implant 10 further includes a display device 14, in communication with the control module 12, which generates a visual display of the image in response to a signal received thereby. Both the control module 12 and the display device 14 are located beneath the skin 16 of a biological host, such as a human. The control module 12 and the display device 14 may be implanted beneath the skin, or alternatively, skin may be grown over the control module 12 and the display device 14.

The subcutaneous implant 10 preferably has a biologically-inert exterior in order to reduce biological interaction with the host. Here, the subcutaneous implant 10 may be coated with a biologically-inert substance, or encapsulated within a biologically-inert capsule.

The display device 14 is located shallowly beneath the skin 16 so that the image displayed thereby is externally viewable. Since the skin 16 of a human is substantially transparent, the display device 14 may comprise either a light-emissive display or a light-absorptive display for generating the externally-viewable image. In a preferred embodiment, the display device 14 includes a liquid crystal display, which is an example of a light-absorptive display. The display device 14 may further include back lighting means for providing illumination of the displayed image.

The control module 12 may be located shallowly beneath the skin 16, although other locations of the control module 12 within the biological host are within the scope of the invention. The control module 12 and the display device 14 communicate signals via an electronic coupling 20. The electronic coupling 20 may comprise, for example, one or more wires or fiber optic links, or simply a direct plug-type connection. Alternatively, the control module 12 may communicate electronic signals to the display device 14 via existing tissue in the biological host.

The display device 14 is flexibly constructed in order to conform to the surface of the skin 16. This allows the display device 14 to be implanted and/or located at a wide variety of positions on the body of the biological host. Further, the flexibility of the display device 14 aids in reducing any discomfort to a human receiving the implant. Similarly, it is preferred that the control module 12 be flexible if implanted and/or located shallowly beneath the skin 16.

The display device 14 is capable of displaying a variety of different images based upon the signal provided by the control module 12. Consequently, the specific image which is displayed may be updated as commanded by the control module 12. As a result, the subcutaneous implant 10 provides an apparatus for displaying at least one of a plurality of different images.

In a preferred embodiment, the display device 14 contains a plurality of picture elements which are selectively displayed in response to the signal provided by the control module 12. For example, the display device 14 can comprise a two-dimensional array of picture elements (i.e. pixels), wherein each of the picture elements is selectively displayed to form a desired image. Alternatively, the display device 14 can comprise a plurality of seven-segment displays for displaying numerical images, or a plurality of similar displays for displaying alphanumerical images. The picture elements contained in the display device 14 may provide a either monochrome image or a color image.

Preferably, the display device 14 is of a sufficient physical size in order to facilitate ease in reading images displayed thereby. In one embodiment, the display device 14 is 1½ inches by 1½ inches and ⅛ inch thick, although different display sizes are within the scope of the invention. The control module 14 is preferably as small as practical. For the purpose of illustration, one embodiment of the present invention has the control module 14 being ¾ inch by ¾ inch and ⅛ inch thick.

Figure 2:
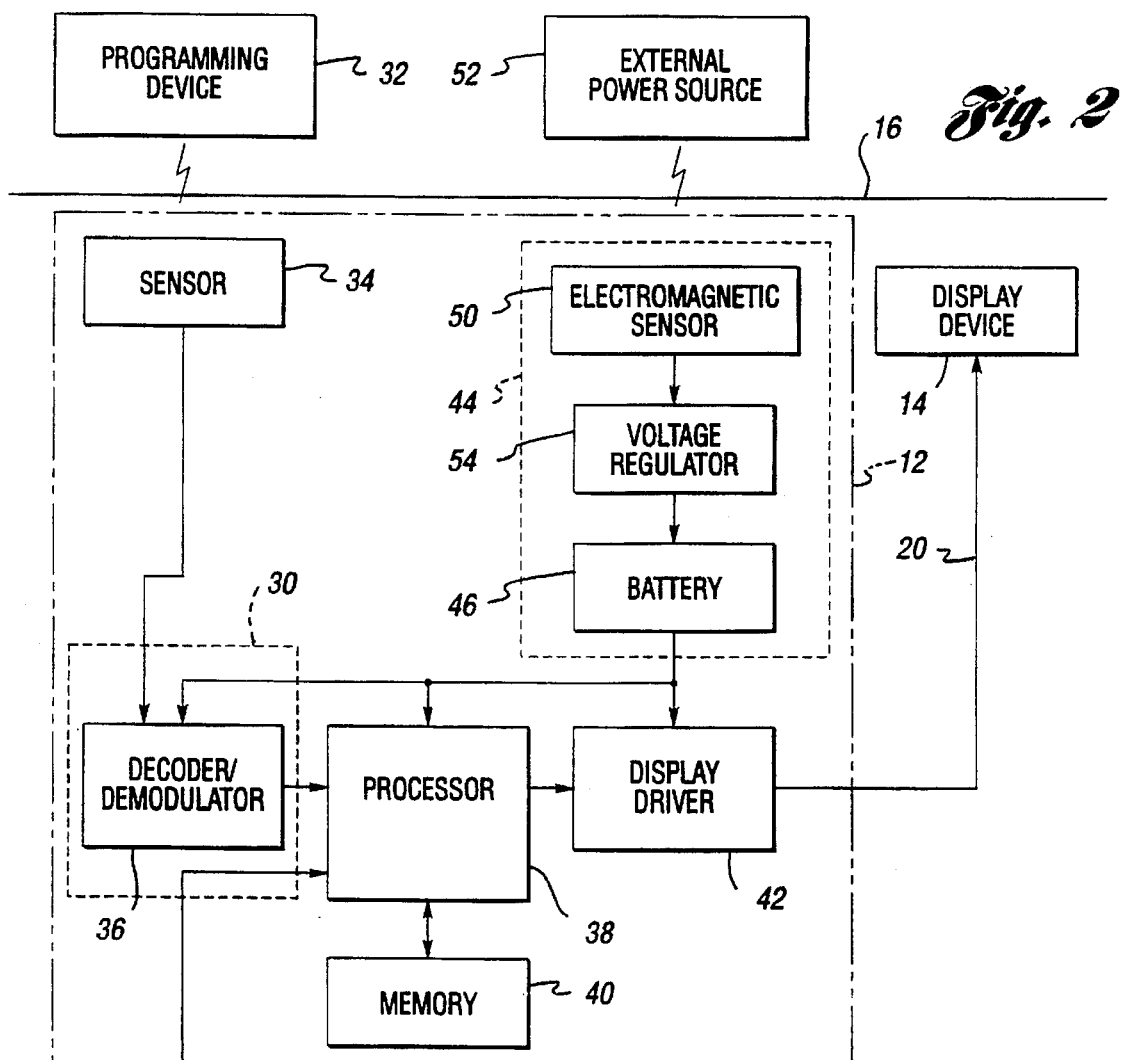
FIG. 2 is a block diagram of an embodiment of the present invention.

Referring now to FIG. 2, there is shown a block diagram of an embodiment of a subcutaneous implant in accordance with the present invention. The control module 12 includes a receiver 30 which receives information from at least one of a variety of sources. The receiver 30 may receive display information and/or programming information from a user or a programmer. The display information may include a signal representative of a decorative pattern, such as an "electronic tatoo", which is to be displayed on the display device 14. Alternatively, the display information may include a signal representative of alphanumerical characters. The alphanumerical characters may provide, for example, identification information and/or medical information. The programming information may include information regarding the manner in which the images are to be displayed. For example, the images may be displayed statically or dynamically.

The display information and/or programming information, in the form of a signal, is transmitted to the receiver 30 by a programming device 32 located exterior to the skin surface 16. The programming device 32 may transmit the information to the receiver 30 by optical means, acoustical means, electrical means, mechanical means, and/ or inductive means, for example. The receiver 30 may include a sensor 34 such as an infrared sensor, an ultrasonic sensor, a radio frequency sensor, an electromagnetic sensor, an optical sensor, and/or an inductive sensor, or the like, to receive the information transmitted by the programming device 32.

In a preferred embodiment, the programming device 32 transmits the display information and/or programming information in the form of frequency modulated (FM) infrared light pulses. The infrared light pulses are transmitted through the skin 16 to the sensor 34, which comprises an infrared sensor, located shallowly beneath the skin 16.

Although it is preferred that the programming information be transmitted to the receiver 30 noninvasively, the receiver 30 may alternatively include a microelectrode port which receives programming information via acupuncture needles, or the like, inserted into the skin. Another alternative is communicate programming information to the receiver 30 via an external port in the skin as is utilized in biomedical sensing applications.

Another source of information for the receiver 30 may be one or more biosensors located and/or implanted within the biological host. The one or more biosensors act as an interface between the biological host and the receiver 30 for detecting and/or measuring at least one physiological property of the biological host. Various types of biosensors, such as physical sensors and chemical sensors, may be utilized. Typically, the biosensors provide the measured information to the receiver 30 in the form of electrical information signals.

The receiver 30 includes a decoder/demodulator 36 which decodes and/or demodulates programming and display information signals received by the sensor 34. In a preferred embodiment, the decoder/demodulator 36 includes a FM demodulator for demodulating the received infrared FM light pulses.

Optionally, the control module 12 includes a processor 38 which communicates with the receiver 30. The processor 38 performs a sequence of programmed steps based upon the information received and demodulated by the receiver 30. The processor 38 can have a digital implementation, such as a microprocessor which performs the programmed steps, or an analog implementation using standard means for performing analog computations.

The processor 38 may, for example, decompress a compressed image signal (representative of display information) received and demodulated by the receiver 30. As another example, the processor 38 may form an image to be displayed on the display device 14 based upon information received from the biosensors. Preferably, the processor 38 is programmed based upon programming information received by the receiver 30. By allowing the processor 38 to be reprogrammed using an external programming device 32, the implant is versatile in performing many display functions.

As a further option, the control module 12 includes a memory 40 in communication with the receiver 30 via the processor 38. The memory 40 provides means for storing the received programming and display information. For example, the memory 40 may be employed to store a sequence of steps to be performed by the processor 38, the steps being provided using the external programming device 32. The memory 40 may also be employed to store images to be displayed on the display device 14. Further, the memory may store information provided by the biosensors. Preferably, the memory 40 includes a nonvolatile memory device, such as an EEPROM or the like, which retains its memory in absence of power applied thereto.

A display driver 42 communicates with the receiver 30 in order to provide signals capable of driving the display device 14. In embodiments utilizing the processor 38, the display device 14 is coupled to the processor 38. As a result, the display device 14 displays an image based upon display information, programming information, and/or biosensing information received by the control module 12. Preferably, the above-described circuit components of the control module 12, namely, the receiver 30, the processor 38, the memory 40, and the display driver 42 are implemented on a small printed circuit board or a small integrated circuit chip.

A power supply 44 provides power to the above-described circuit components within the control module 12. Preferably supply 44 includes a battery 46, such as a small, long life rechargeable battery. The power supply 44 may include an electromagnetic sensor 50 which allows an external power source 52 to be inductively coupled thereto. A voltage regulator 54 may also be included in the power supply 44 to convert an alternating current signal received by the electromagnetic sensor 50 to a direct current signal used to power the control module 12.

Using a preferred embodiment of the power supply 44, the external power source 52 may be used to directly power the components of the control module 12 in place of the battery 46. Further, the external power source 52 may be used to recharge the battery 46.

Figure 3:
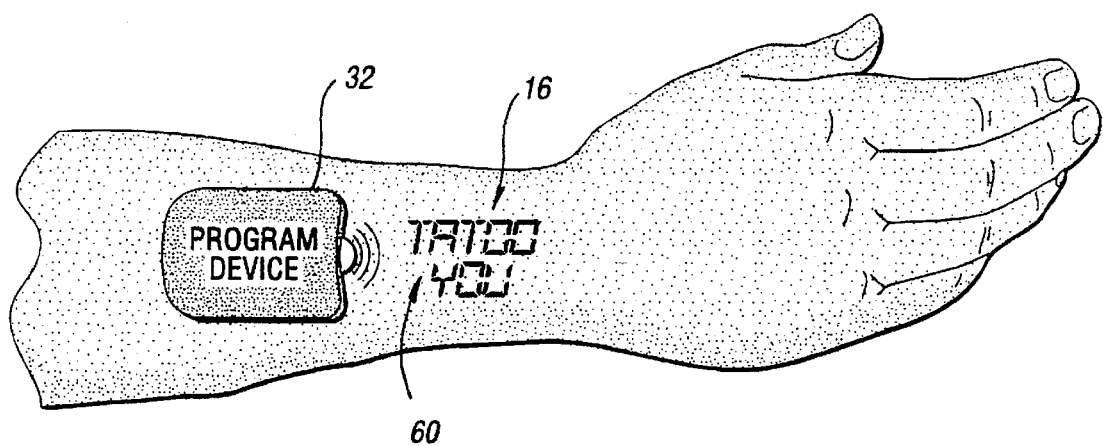
FIG. 3 is an illustration of an application of an embodiment of the present invention.

The externally-viewable image displayed by the display device 14 can be utilized in a wide variety of applications. FIG. 3 illustrates one such application wherein the biological host is a human. A subcutaneous implant (not specifically illustrated) is located beneath the skin surface 16 near the wrist of the human. The implant includes a flexible LCD display which conforms beneath the skin surface 16. The LCD display has a two-dimensional array of pixels which are selectively activated to form an image.

The implant receives display information via infrared signals transmitted by the programming device 32. The display information includes a pixel-by-pixel representation of the image to be displayed on the LCD. The display information may be compressed to reduce the time required to transmit the display information from the programming device 32.

The LCD displays the image based upon the received display information. The displayed image acts to alter the surface appearance of the skin to produce the desired externally-viewable display 60. The externally-viewable display may be modified by a subsequent transmission of display information using the programming device 32. Hence, embodiments of the present invention may be utilized to forman electronic, reprogrammable tatoo. It is anticipated that the implant may be employed in a wide variety of decorative or cosmetic applications.

Figure 4:
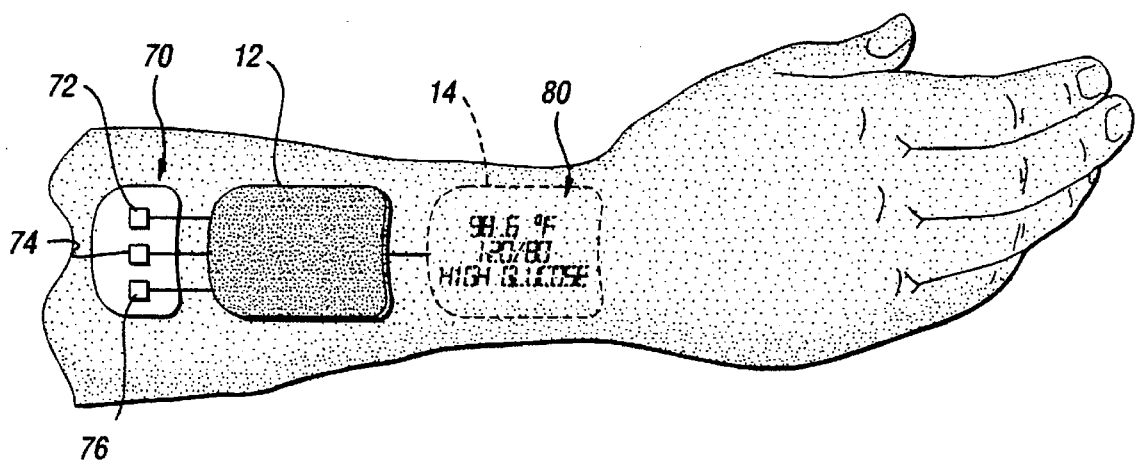
FIG. 4 is an illustration of an embodiment of the present invention for use in another application.

In another application, as illustrated in FIG. 4, the control module 12 communicates with at least one biosensor 70 implanted within the biological host. The biosensor 70 acts as an interface between the biological host and the implant 10 for detecting and/or measuring at least one physiological property of the biological host.

The control module 12 receives signals representative of measurements from the biosensor 70, processes the signals, and produces a signal representative of an image based upon the measurements. The image based upon the measurements is displayed on the display device 14 for external view. This embodiment allows internal vital signs of a human to be displayed in, for example, a numerical or an alphanumerical form. For the purpose of illustration, the at least one biosensor 70 includes a temperature sensor 72, a blood pressure sensor 74, and a blood analyzer sensor 76. As such, the image includes an alphanumerical display 80 of the temperature, the blood pressure, and the results of the blood analysis of the individual. Alternatively, the measured physiological quantities may be displayed graphically. For example, the temperature may be displayed by a graphical representation of a thermometer.

The above-described embodiments of the present invention have many advantages. By employing a programmable control module, embodiments of the present invention may be programmed to provide general information such as time, date, periodic scheduling matters and the like. Moreover, the control module can be programmed to change the image displayed at desired intervals. For example, certain images would be displayed at predetermined times or on predetermined days. Further, embodiments of the present invention may be programmed to provide identification data or medical information data. The implant may be utilized in animals for providing identification data, as well as other relevant information concerning feeding and caring procedures.

Another advantage is that embodiments of the present invention are capable of being reprogrammed at a later date in order to erase or change the information to be displayed. The reprogramming can be accomplished noninvasively as is illustrated in a preferred embodiment. By including an magnetic power sensor along with a rechargeable battery, an embodiment of the implant may be repeatedly recharged to extend its lifetime.

A further advantage is that conventional medical and surgical techniques and procedures can be used to implant embodiments of the present invention into the biological host. Preferably, technique is similar to those used to implant medical aids and accessories, such as pacemakers, hearing aids, or the like, could be used. It is anticipated that the implant could be performed for a human in a simple outpatient procedure at a doctor's office.

Embodiments of the present invention have a wide variety of possible uses and applications, both for humans and for animals. These applications include medical applications and identification applications. Alternatively, embodiments of the present invention may be used to generate an aesthetic display to form an electronic, programmable tatoo. In general, various logos, tatoos, names, or the like can be displayed.

It is noted that the general principle of the subcutaneous implant may be applied to other senses. For example, instead of providing a visual display, the implant may generate heat or vibration within an individual for purposes of pleasure, comfort, or information presentation.

It should be noted that the present invention may be used in a wide variety of different constructions encompassing many alternatives, modifications, and variations which are apparent to those with ordinary skill in the art. Accordingly, the present invention is intended to embrace all such alternatives, modifications, and variations as fall within the spirit and broad scope of the appended claims.

What is claimed is:

1. An implant for subcutaneous insertion beneath a skin surface, the implant comprising:

a control module adapted to be located beneath the skin surface, the control module providing a display signal representative of an image to be displayed; and a display device adapted to be located beneath the skin surface, the display device displaying the image through the skin surface based upon the display signal.

2. The implant of claim 1 wherein the control module includes a battery for powering the implant.

3. The implant of claim 2 wherein the control module includes a magnetic sensor for recharging the battery from an external power source.

4. The implant of claim 2 wherein the control module includes a magnetic sensor for powering the implant from an external power source.

5. The implant of claim 1 wherein the control module includes a receiver which receives information used in forming the display signal.

6. The implant of claim 5 wherein the information includes display information.

7. The implant of claim 5 wherein the information includes programming information.

8. The implant of claim 7 wherein the control module includes a microprocessor which performs a sequence of programmed steps to form the image, wherein the sequence of programmed steps are based upon the programming information received by the receiver.

9. The implant of claim 5 further comprising a sensor which receives a signal representative of the information, wherein the receiver is responsive to the sensor.

10. The implant of claim 9 wherein the receiver includes a decoder coupled to the sensor, the decoder decoding the signal representative of the information.

11. The implant of claim 5 further comprising an infrared sensor which receives an infrared signal representative of the information, the infrared signal being transmitted from a location exterior to the skin surface.

12. The implant of claim 11 wherein the infrared signal is a frequency modulated (FM) signal.

13. The implant of claim 12 wherein the receiver includes a FM decoder coupled to the sensor, the FM decoder decoding the infrared signal representative of the information.

14. The implant of claim 1 wherein the display device includes a liquid crystal display.

15. The implant of claim 14 wherein the liquid crystal display contains a two-dimensional array of pixels which are selectively activated based upon the display signal.

16. The implant of claim 1 wherein the control module includes a microprocessor which performs a sequence of programmed steps to form the image.

17. The implant of claim 1 further comprising means for backlighting the display device.

18. An implant for subcutaneous insertion beneath a skin surface, the implant comprising:

a sensor which receives a signal representative of information used to form an image, the signal transmitted from a location exterior to the skin surface, the information containing at least one of programming information and display information;

a decoder, operatively associated with the sensor, which decodes the signal;

a processor, operatively associated with the decoder, the processor forming an image signal using a sequence of programmed steps, wherein the programmed steps are based upon the programming information received by the sensor;

a display driver operatively associated with said processor and which produces a display signal in dependence upon the image signal formed by the processor; and a display device adapted to be located shallowly beneath the skin surface, the display device operatively associated with said display driver and adapted to display the image through the skin surface based upon the display signal.

19. An implant for subcutaneous insertion beneath a skin surface, the implant comprising:

an infrared sensor which receives an infrared signal representative of information used to form an image, the infrared signal transmitted from a location exterior to the skin surface, the information containing at least one of programming information and display information;

a frequency modulation decoder, operatively associated with the infrared sensor, which decodes the infrared signal;

a processor operatively associated with the decoder, the processor forming an image signal using a sequence of programmed steps, wherein the programmed steps are based upon the programming information received by the infrared sensor;

a display driver operatively associated with the processor and which produces a display signal in dependence upon the image signal formed by the processor; and a liquid crystal display adapted to be located shallowly beneath the skin surface, the liquid crystal display operatively associated with said display driver and having a two-dimensional array of pixels which are selectively activated based upon the display signal, whereby the display device is adapted to display the image through the skin surface.

\* \* \* \* \*